(12) United States Patent
Swinnen et al.

(10) Patent No.: US 7,479,575 B2
(45) Date of Patent: Jan. 20, 2009

(54) METHOD FOR PREPARING PARA-PHENYL ALKYNYL BENZALDEHYDES

(75) Inventors: Dominique Swinnen, Beaumont (FR); Danig Pohin, Saint-Julien-en-Genevois (FR)

(73) Assignee: Laboratoires Serono SA, Vaud (CH)

( * ) Notice: Subject to any disclaimer, the term of this patent is extended or adjusted under 35 U.S.C. 154(b) by 0 days.

(21) Appl. No.: 10/575,266

(22) PCT Filed: Oct. 12, 2004

(86) PCT No.: PCT/EP2004/052515

§ 371 (c)(1),
(2), (4) Date: Nov. 30, 2007

(87) PCT Pub. No.: WO2005/037758

PCT Pub. Date: Apr. 28, 2005

(65) Prior Publication Data

US 2008/0108849 A1     May 8, 2008

(30) Foreign Application Priority Data

Oct. 13, 2003    (EP)   ................... 03103780

(51) Int. Cl.
*C07C 45/00*      (2006.01)
(52) U.S. Cl. ...................................... 568/437
(58) Field of Classification Search .................. 568/437
See application file for complete search history.

(56) References Cited

FOREIGN PATENT DOCUMENTS

| GB | 1 581 359 | 12/1980 |
|---|---|---|
| JP | 7-138196 | 5/1995 |
| WO | 03/064376 | 8/2003 |

OTHER PUBLICATIONS

Gee Kyle R. et al., "10,5-(Iminomethano)-10,11-dihydro-5 H-dibenzo [a,d] cycloheptene and Derivatives. Potent PCP Receptor Ligands", J. Med. Chem., vol. 36, No. 14, pp. 1938-1946, 1993.

Database Beilstein Beilstein Institute for Organic Chemistry, Frankfurt-Main, De; XP002272673, See BRN 9202297 & S.V. Klyatskaya et al,: Russ. Chem. Bl., vol. 51, No. 1, pp. 128-134, 2002.

Lubczyk, Veronika et al., "Investigations on Estrogen Receptor Binding. The Estrogenic, Antiestrogenic, and Cytotoxic Properties of C2-Alkyl-Substituted 1,1-Bis (4-hydroxyphenyl)-2-phenylethenes", J. Med. Chem., vol. 45, No. 24, pp. 5358-5364, 2002.

*Primary Examiner*—Sikarl A Witherspoon
(74) *Attorney, Agent, or Firm*—Oblon, Spivak, McClelland, Maier & Neustadt, P.C.

(57) ABSTRACT

The present invention is related to a new synthesis for preparing para-phenyl alkynyl benzaldehyde of general formula (I). The compounds of formula (I) are useful building blocks, in particular in the synthesis of electrically conducting polymers. R is selected from the group consisting of $C_1$-$C_{12}$-alkyl, $C_1$-$C_{12}$-alkyl aryl, $C_1$-$C_{12}$-alkyl heteroaryl, $C_2$-$C_{12}$-alkenyl, $C_2C_{12}$-alkenyl aryl, $C_2$-$C_{12}$-alkenyl heteroaryl, $C_2$-$C_{12}$-alkynyl, $C_2$-$C_{12}$-alkynyl aryl, $C_2$-$C_{12}$-alkynyl heteroaryl, $C_3$-$C_8$-cycloalkyl$C_1$-$C_{12}$-alkyl-$C_3$-$C_8$-cycloalkyl, $C_1$-$C_{12}$-alkoxy, aryl, heteroaryl, halides.

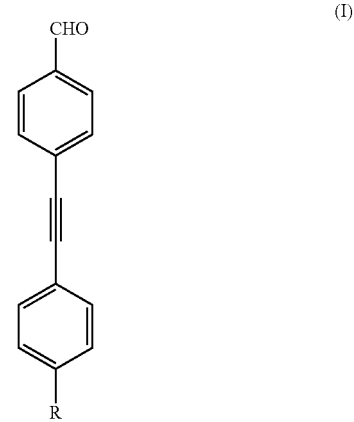

14 Claims, No Drawings

METHOD FOR PREPARING PARA-PHENYL ALKYNYL BENZALDEHYDES

SUMMARY OF THE INVENTION

The present invention is related to a new synthesis for preparing para-phenyl alkynyl benzaldehyde of general formula (I). The compounds of formula (I) are useful building blocks, in particular in the synthesis of drugs and electrically conducting polymers.

FIELD OF THE INVENTION

The present invention is related to a new synthesis for preparing para-phenyl alkynyl benzaldehydes of general formula (I):

(I)

R is selected from the group consisting of $C_1$-$C_{12}$-alkyl, $C_1$-$C_{12}$-alkyl aryl, $C_1$-$C_{12}$-alkyl heteroaryl, $C_2$-$C_{12}$-alkenyl, $C_2$-$C_{12}$-alkenyl aryl, $C_2$-$C_{12}$-alkenyl heteroaryl, $C_2$-$C_{12}$-alkynyl, $C_2$-$C_{12}$-alkynyl aryl, $C_2$-$C_{12}$-alkynyl heteroaryl, $C_1$-$C_{12}$-alkyl-$C_3$-$C_8$-cycloalkyl, $C_3$-C8-cycloalkyl, $C_1$-$C_{12}$-alkoxy, aryl, heteroaryl, halides.

The method employs commercially available, or easily obtainable, starting compounds and comprises or consists of four steps.

BACKGROUND OF THE INVENTION

The synthetic approach for preparing para-phenyl alkynyl benzaldehydes is well known. Several documents quote the use of para-phenyl alkynyl benzaldehydes as building block in the synthesis of various compounds, e.g. for the synthesis of electrically conductive polymers.

A Japanese application (JP 07138196, published on 30 May 1995), for instance, describes the following specific method. The method involves the use of a Palladium catalyst in two separate steps.

Scheme 1

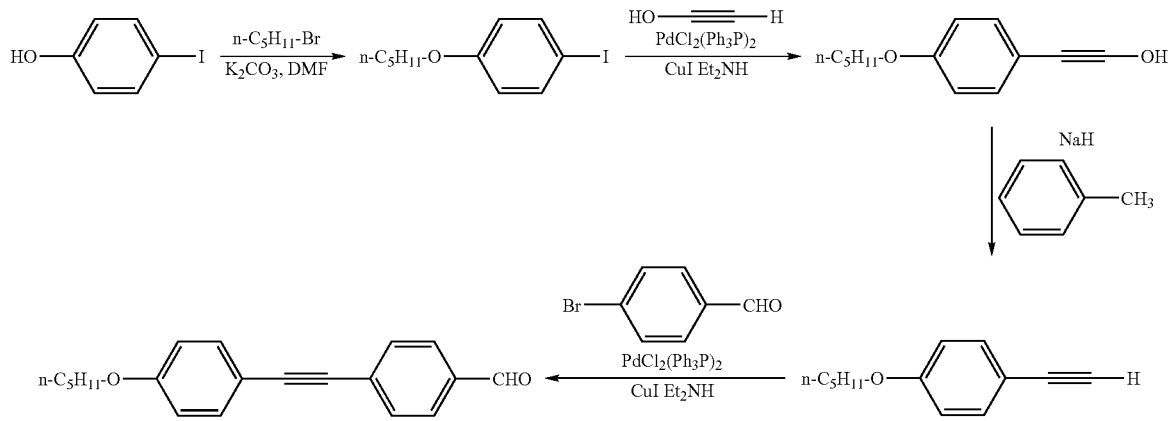

A further application related to para-phenyl alkynyl benzaldehyde, is PCT/EPO3/00808 (priority date: 29 Jan. 2002). It also implies the use of a palladium catalyst and discloses the following specific pathway for synthesizing para-phenyl alkynyl benzaldehyde:

Scheme 2

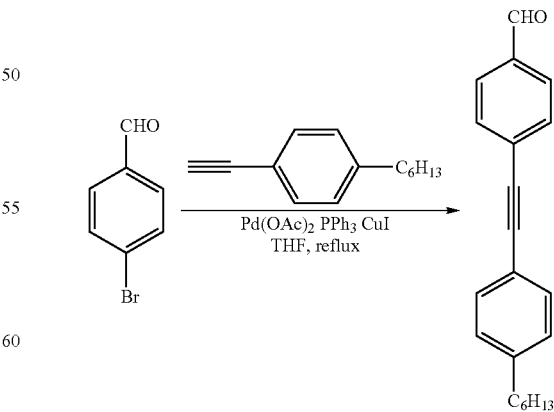

The methods used in the art imply the use of costly Palladium catalysts. Furthermore, the use of Palladium catalysts causes Palladium contamination and frequently, formation of undesired by-products. The present invention provides a new method that does not require the use of Palladium catalysts.

DESCRIPTION OF THE INVENTION

The present invention allows to overcome the above said problems by a synthesis that involves four steps and moreover uses, as starting compounds, compounds that may be easily synthesized or are commercially available.

The following paragraphs provide definitions of the various chemical moieties that make up the compounds according to the invention and are intended to apply uniformly throughout the specification and claims unless an otherwise expressly set out definition provides a broader definition.

"$C_1$-$C_{12}$-alkyl" refers to alkyl groups having 1 to 12 carbon atoms. This term is exemplified by groups such as methyl, ethyl, n-propyl, isopropyl, n-butyl, isobutyl, tert-butyl, n-hexyl, heptyl, octyl, nonyl and the like.

"$C_1$-$C_{12}$-alkyl aryl" refers to $C_1$-$C_{12}$-alkyl groups having an aryl substituent, including benzyl, phenethyl and the like.

"Aryl" refers to an unsaturated aromatic carbocyclic group of from 6 to 14 carbon atoms having a single ring (e.g., phenyl) or multiple condensed rings (e.g., naphthyl). Preferred aryl include phenyl, naphthyl, phenantrenyl and the like.

"Heteroaryl" refers to a monocyclic heteroaromatic, or a bicyclic or a tricyclic fused-ring heteroaromatic group. Particular examples of heteroaromatic groups include optionally substituted pyridyl, pyrrolyl, furyl, thienyl, imidazolyl, oxazolyl, isoxazolyl, thiazolyl, isothiazolyl, pyrazolyl, 1,2,3-triazolyl, 1,2,4-triazolyl, 1,2,3-oxadiazolyl, 1,2,4-oxadiazolyl, 1,2,5-oxadiazolyl, 1,3,4-oxadiazolyl, 1,3,4-triazinyl, 1,2,3-triazinyl, benzofuryl, [2,3-dihydro]benzofuryl, isobenzofuryl, benzothienyl, benzotriazolyl, isobenzothienyl, indolyl, isoindolyl, 3H-indolyl, benzimidazolyl, imidazo[1,2-a]pyridyl, benzothiazolyl, benzoxa-zolyl, quinolizinyl, quinazolinyl, pthalazinyl, quinoxalinyl, cinnolinyl, napthyridinyl, pyrido[3,4-b]pyridyl, pyrido[3,2-b]pyridyl, pyrido[4,3-b]pyridyl, quinolyl, isoquinolyl, tetrazolyl, 5,6,7,8-tetrahydroquinolyl, 5,6,7,8-tetrahydroisoquinolyl, purinyl, pteridinyl, carbazolyl, xanthenyl or benzoquinolyl.

"Halogen" refers to fluoro, chloro, bromo and iodo atoms.

"$C_1$-$C_{12}$-alkyl heteroaryl" refers to $C_1$-$C_{12}$-alkyl groups having a heteroaryl substituent, including 2-furylmethyl, 2-thienylmethyl, 2-(1H-indol-3-yl)ethyl and the like.

"$C_2$-$C_{12}$-alkenyl" refers to alkenyl groups preferably having from 2 to 12 carbon atoms and having at least 1 or 2 sites of alkenyl unsaturation. Such alkenyl groups include ethenyl (—CH=$CH_2$), n-2-propenyl (allyl, —$CH_2$CH=$CH_2$) and the like.

"$C_2$-$C_{12}$-alkenyl aryl" refers to $C_2$-$C_{12}$-alkenyl groups having an aryl substituent, including 2-phenylvinyl and the like.

"$C_2$-$C_{12}$-alkenyl heteroaryl" refers to $C_2$-$C_{12}$-alkenyl groups having a heteroaryl substituent, including 2-(3-pyridinyl)vinyl and the like.

"$C_2$-$C_{12}$-alkynyl" refers to alkynyl groups preferably having from 2 to 12 carbon atoms and having at least 1-2 sites of alkynyl unsaturation, preferred alkynyl groups include ethynyl (—C≡CH), propargyl (—$CH_2$C≡CH), and the like.

"$C_2$-$C_{12}$-alkynyl aryl" refers to $C_2$-$C_{12}$-alkynyl groups having an aryl substituent, including phenylethynyl and the like.

"$C_2$-$C_{12}$-alkynyl heteroaryl" refers to $C_2$-$C_{12}$-alkynyl groups having a heteroaryl substituent, including 2-thienylethynyl and the like.

"$C_3$-$C_8$-cycloalkyl" refers to a saturated carbocyclic group of from 3 to 8 carbon atoms having a single ring (e.g., cyclohexyl) or multiple condensed rings (e.g., norbornyl). Preferred cycloalkyl include cyclopentyl, cyclohexyl, norbornyl and the like.

"$C_1$-$C_{12}$-alkyl cycloalkyl" refers to $C_1$-$C_{12}$-alkyl groups having a cycloalkyl substituent, including cyclohexylmethyl, cyclopentylpropyl, and the like.

"Alkoxy" refers to the group —O—R where R includes "$C_1$-$C_6$-alkyl", "$C_2$-$C_6$-alkenyl", "$C_2$-$C_6$-alkynyl", "$C_3$-$C_8$-cycloalkyl", "heterocycloalkyl", "aryl", "heteroaryl", "$C_1$-$C_6$-alkyl aryl" or "$C_1$-$C_6$-alkyl heteroaryl", "$C_2$-$C_6$-alkenyl aryl", "$C_2$-$C_6$-alkenyl heteroaryl", "$C_2$-$C_6$-alkynyl aryl", "$C_2$-$C_6$-alkynylheteroaryl", "$C_1$-$C_6$-alkyl cycloalkyl", "$C_1$-$C_6$-alkyl heterocycloalkyl".

The method, according to the present invention, comprises or consists of the following steps 1 to 4:

According to the invention the building block of formula (I) can be prepared starting either from compound of general formula (II) or from compound of general formula (III) wherein LG is a suitable leaving group. Compounds (II) and (III) (e.g. bromide, chloride, iodide) are commercially available or may be prepared according to known techniques.

Step 1: An acyl chloride (III) is coupled with a substituted benzene of formula (IV), wherein R is selected from the group consisting of $C_1$-$C_{12}$-alkyl, $C_1$-$C_{12}$-alkyl aryl, $C_1$-$C_{12}$-alkyl heteroaryl, $C_2$-$C_{12}$-alkenyl, $C_2$-$C_{12}$-alkenyl aryl, $C_2$-$C_{12}$-alkenyl heteroaryl, $C_2$-$C_{12}$-alkynyl, $C_2$-$C_{12}$-alkynyl aryl, $C_2$-$C_{12}$-alkynyl heteroaryl, $C_3$-$C8$-cycloalkyl, $C_1$-$C_{12}$-alkoxy, aryl, heteroaryl or a halide, thus yielding a ketone of formula (V).

LG is a suitable leaving group like a halide (Br, Cl, I).

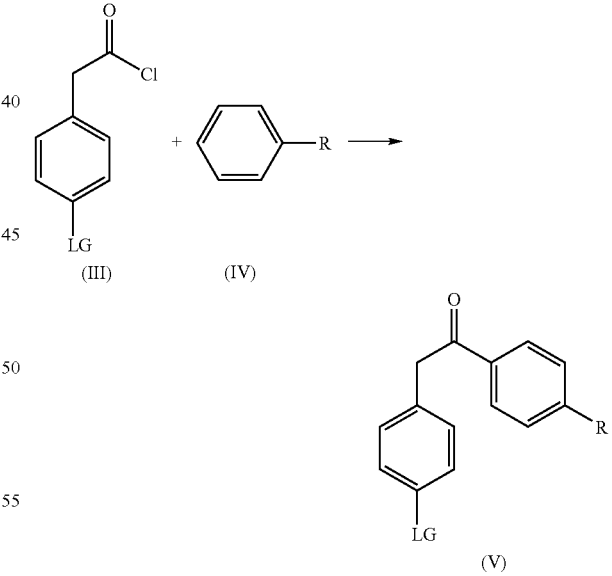

Scheme 3

Preferably, the reaction is performed in the presence of a Lewis acid (for example $FeCl_3$, $AlCl_3$) in a range of temperature from room temperature to 50° C., typically for a period of about 5 hours.

The acyl chloride starting compound (III) in Scheme 3 is typically obtained by reaction of the acid (II) with a suitable chlorinating agent, e.g. thionyl chloride, oxalyl chloride, $PCl_3$ or $PCl_5$

Scheme 4

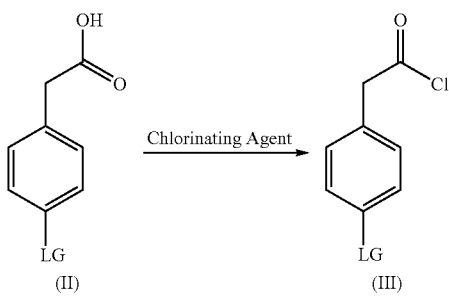

Step 2: Then, the compound of formula (V) is transformed into compound (VI) using a suitable halogenating agent including acyl chlorides, e.g. acetyl chloride, bromide.

Scheme 5

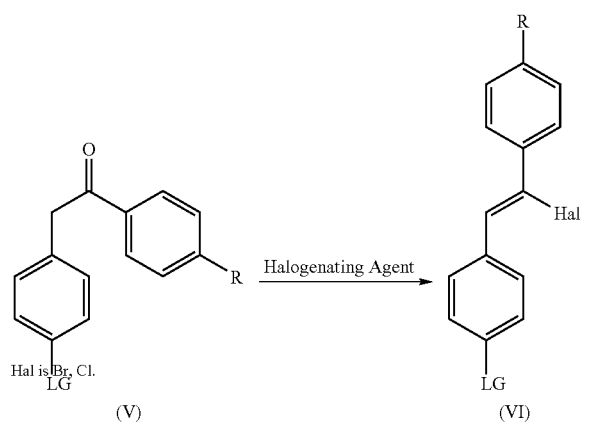

Preferably, the reaction is performed with an acyl chloride in an acidic organic solvent (TFA or methane sulfonic acid) preferentially TFA at room temperature, typically for a period of 40 hours.

Step 3: The compound (VI) is then transformed into compound (VII) by eliminating is HCl, preferably in an alkaline medium (dehydrohalogenation).

Scheme 6

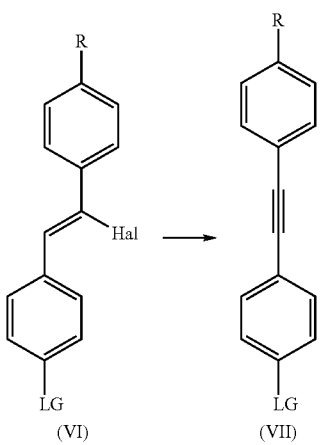

Preferably the reaction is performed in an organic solvent (for example a mixture of dioxane and methanol), typically in presence of a base (preferred bases include NaOH and KOH), at a temperature of 80° C., typically for a period of 20 hours.

Step 4: In a final step, a compound of formula (VII) is reacted with a formylating agent (VIII) to give compound (I). In one embodiment, a compound of formula (VII), wherein LG is a halide, is first transformed into an activated species, e.g. an organometallic derivative, such as organo-magnesium or organo-lithium using magnesium or butyl lithium respectively. The activated species, e.g. the organo-metallic derivative, is then transformed into the aldehyde of formula (I) by reaction with a formylating agent such as DMF, 1-formyl-piperidine, 1-formyl piperazine, N-methyl-N-(2-pyridyl) formamide, N-methyl formanilide, Weinreb formamide (e.g: N-methoxy-N-methylformamide). The two steps protocol can be performed in one pot or successively.

In one embodiment, a compound (VII) is provided; Mg in an organic solvent such as THF as well as 1-formyl-piperidine are added in order to perform a one-pot reaction.

In a further embodiment compound (VII) is provided; n-butyl lithium in THF as well as DMF as formylating agent are added in order to perform a one-pot reaction.

Scheme 7

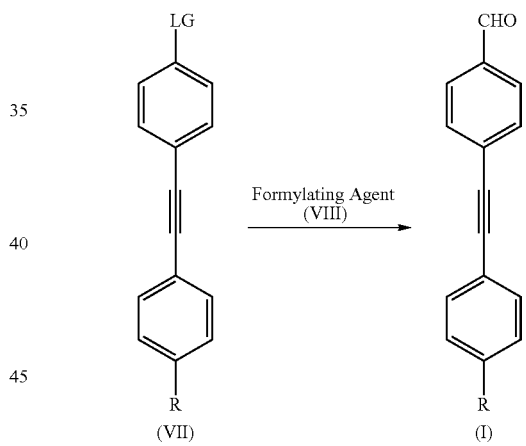

In a specific embodiment, the novel method allows the preparation of compounds according to formula (I), wherein R is $C_1$-$C_6$ -alkyl (e.g. methyl, ethyl, n-propyl, isopropyl, n-butyl, isobutyl, tert-butyl, n-hexyl, moiety).

The new synthetic approach for preparing the compounds of formula (I) has the advantage that it does not involve the use of palladium.

The present invention shall be illustrated by means of the following examples. It will be appreciated that where typical or preferred experimental conditions (i.e., reaction temperatures, time, moles of reagents, solvents, etc.) are given, other experimental conditions can also be used unless otherwise stated. Optimum reaction conditions may vary with the particular reactants or solvents used, but such conditions can be determined by one skilled in the art by routine optimization procedures.

EXAMPLE 1

Preparation of 4-(4-methoxy-phenylethynyl)-benzaldehyde a) Synthesis of (4bromo-phenyl)-acetyl chloride (IIIa)

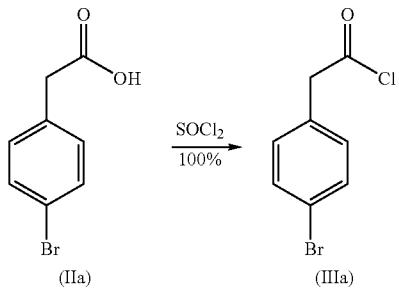

In a 1 L flask, topped with an HCl trap, SOCl$_2$ (495 ml; 3 vols) was added into (4-bromo-phenyl)-acetic acid (IIa) (165 g; 767.28 mmol). The reaction mixture was stirred at 60° C. for 3 h. Then, it was concentrated under vacuum and co-evaporated with toluene (100 mL). The resulting light brown oil was dried under vacuum for 48 h protected from the light using an aluminum foil. The title compound (m=178.20 g) was obtained as oil in a yield of 99.5%.

b) Step 1: Synthesis of 2-(4-bromophenyl)-1-(4-methoxyphenyl) ethanone (Va)

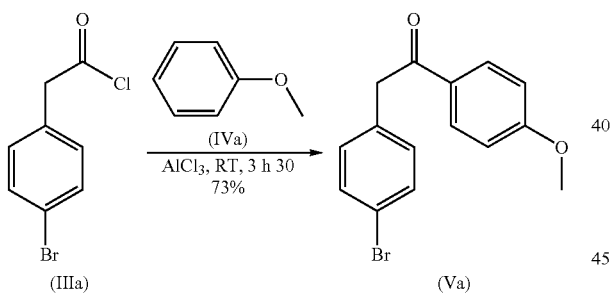

To a 50 mL three-necked flask containing AlCl$_3$ (4.406 g; 33.05 mmol) under N$_2$, anisole (IVa) (4.467 g; 41.31 mmol) was added in one portion at RT. The reaction was exothermic. To this suspension (4-bromo-phenyl)-acetyl chloride (IIIa) (6.430 g; 27.54 mmol) was added drop wise keeping temperature below 20° C. Then the resulting red suspension was stirred at RT for 3h30. The red thick solution was poured under stirring into a mixture of ice and 1N HCl (100 mL), then the resulting white solid was filtered, and washed with water. The solid was washed with pentane (3×30 mL) and dried under vacuum at RT to give a white powder (m=8.51 g). Purification was performed by crystallization from acetone (30 ml) to give the title compound as a white powder (m=6.113 g) in a 73% yield.

1H-NMR (CDCl3=7.26 ppm): 7.97 (d, J=8.85 Hz, 2H), 7.44 (d, J=8.28 Hz, 2H), 7.13 (d, J=8.28 Hz, 2H), 6.93 (d, J=8.85 Hz, 2H), 4.18 (s, 2H), 3.86 (s, 3H)

Melting point: 142° C.

c) Step 2: Synthesis of 4-[(Z)-2-(4-bromophenyl)-1-chlorovinyl] phenyl methyl ether (VIa)

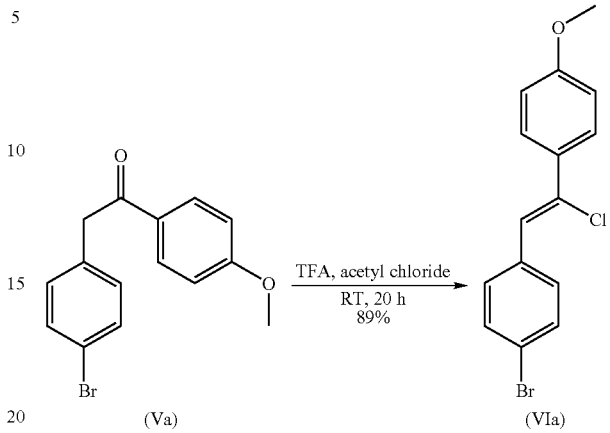

In a 100 mL flask, TFA (15 mL; 197.30 mmol) and acetyl chloride (11.17 mL; 157.81 mmol) were added in one portion into 2-(4-bromophenyl)-1-(4-methoxyphenyl) ethanone (Va) (6.02 g; 19.73 mmol) at RT. Pink reaction mixture was vigorously stirred at RT for 20 h. The resulting brown suspension was cooled to 0° C., filtered and washed with TFA (2×10 mL). The off-white solid was dried under vacuum at 30° C. The title compound (m=5.688 g) was obtained in a 89% yield. Melting point: 97° C.

1H-NMR (CDCl3=7.26 ppm): 7.60 (t, J=8.94 Hz, 4H), 7.50 (d, J=8.66 Hz, 2H), 6.92 (d, io J=8.85 Hz, 2H), 6.89 (s, 1H), 3.85 (s, 3H)

d) Step 3: Synthesis of 4-[(4-bromophenyl) ethynyl] phenyl methyl ether (VIIa)

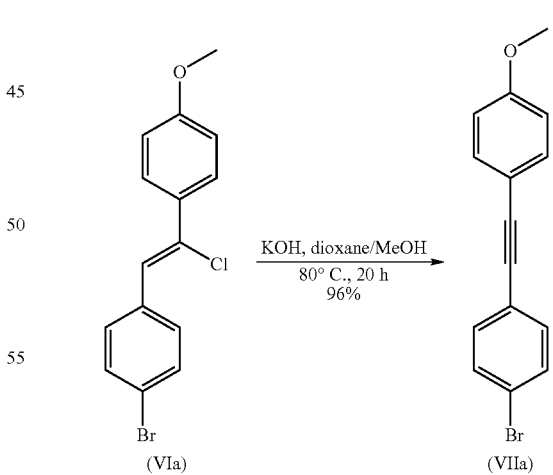

To a 100 mL flask containing a solution of 4-[(Z)-2-(4-bromophenyl)-1-chlorovinyl] phenyl methyl ether (VIa) (5.613 g; 17.34 mmol) in 1,4-dioxane (28 mL; 5 vols) and MeOH (8 mL; 1.4 vols), KOH (1.946 g; 34.69 mmol) was added in one portion. Reaction mixture was stirred at 80° C. overnight. Reaction mixture was taken up in water (200 mL)

and the resulting suspension was filtered and washed with water to give a white solid. Drying under vacuum at 33° C. overnight gave the title compound (m=4.786 g) in a 96% yield. Melting point: 152° C.

1H-NMR (CDCl3=7.26ppm): 7.40 (d, J=2.26 Hz, 2H), 7.37 (d, J=2.26 Hz, 2H), 7.28 (d, J=8.47 Hz, 2H), 6.80 (d, J=8.85 Hz, 2H), 3.75 (s, 3H)

e) Step 4: Synthesis of 4-[(4-methoxyphenyl) ethynyl] benzaldehyde (Ia)

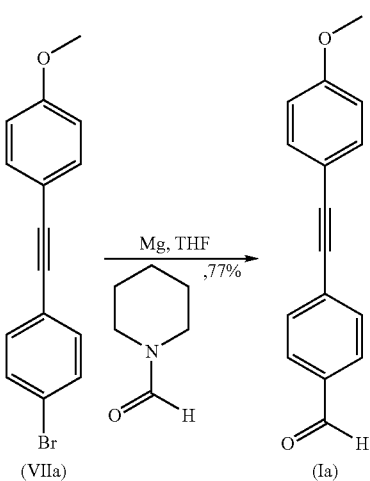

To a dry 100 mL three-necked flask containing magnesium turnings (0.447 g; 18.38 mmol) in dry THF (8 mL), a small portion of 4-[(4-bromophenyl) ethynyl] phenyl methyl ether (VIIa) (0.300 g; 1.044 mmol) was added in one portion, at reflux under a flow of $N_2$. $N_2$ flow and stirring were stopped. The reaction mixture was heated at reflux for 5 minutes then iodine crystals were added, while reflux is maintained to start the reaction. A solution of remaining amount of 4-[(4-bromophenyl) ethynyl] phenyl methyl ether (VIIa) (4.5 g; 15.67 mmol) in dry THF (30 mL) was added drop wise into the reaction mixture while keeping gentle reflux. Reflux was maintained for 15 minutes then temperature was allowed to cool to RT under stirring for 1 h. The reaction mixture was cooled to 3° C. and a solution of dry 1-formyl-piperidine (2.8 mL; 25.07 mmol) in dry THF (10 mL) was added drop wise maintaining temperature at 5° C. The reaction mixture was then allowed to warm to RT and it was stirred overnight. The reaction mixture was cooled to 18° C. and 3N HCl (30 mL) was added. Water was added (50 mL) and extraction was performed with MTBE (50 mL×3). Organic phase was washed successively with water (50 mL×2), saturated solution of $NaHCO_3$ (50 mL×1) and brine (50 mL×1). It was then dried over $MgSO_4$, filtered and concentrated to give a yellow solid. It was taken up in Pet ether (40 mL) and left at 4° C. After 16 h the suspension was filtered and washed with Pet ether (2×30 mL) to give after drying under vacuum a clear yellow solid. The title compound was obtained (m=3.06 g) in a 77% yield. Melting point: 106° C.

1H-NMR (CDCl3=7.26 ppm): 10.0 (s, 1H), 7.85 (d, J=8.28 Hz, 2H), 7.64 (d, J=8.28 Hz, 2H), 7.49 (d, J=8.85 Hz, 2H), 6.90 (d, J=8.85 Hz, 2H), 3.84 (s, 3H)

EXAMPLE 2

Preparation of 4-(4-hexyl-phenylethynyl)-benzaldehyde a) Step 1: Synthesis of 2-(4-bromo-phenyl)-1-(4-hexyl-phenyl)-ethanone (Vb)

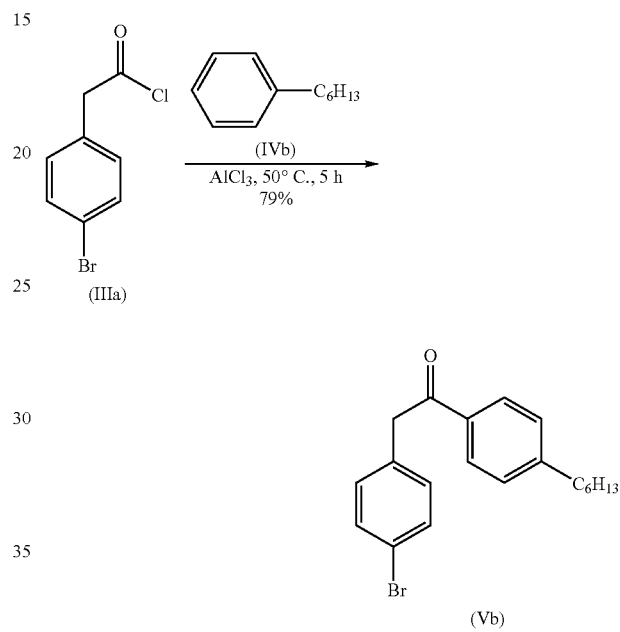

To a 2 L three-necked flask, set up with a mechanical stirring, containing $AlCl_3$ (85.661 g; 642.42 mmol) under $N_2$, 4-hexylbenzene (IVb) (104.25 g; 642.42 mmnol) was added in one portion at room temperature. To this resulting orange suspension (4-bromo-phenyl)-acetyl chloride (IIIa) (125.000 g; 535.35 mmol) was added drop wise during 45 minutes without cooling. Then reaction mixture was stirred for 3 h until temperature cooled down to room temperature, time when no more foaming was observed. The deep brown mixture was then stirred at room temperature overnight. The black thick solution was poured under stirring into a mixture of ice and 1N HCl (800 mL), then the resulting white-orange solid was filtered, and washed successively with water, saturated solution of $NaHCO_3$ and finally with water until pH of the filtrate was 7. The solid was washed with heptane (3×200 mL) and dried under vacuum at room temperature to give the title compound as a white powder (m=151.15 g) in a 79% yield. Melting point: 108° C.

1H-NMR (CDCl3=7.26 ppm): 7.91 (d, J=8.28 Hz, 2H), 7.44 (d, J=8.28 Hz, 2H), 7.26 (d, J=8.28 Hz, 2H), 7.13 (d, J=8.47 Hz, 2H), 4.21 (s, 2H), 2.65 (t, J=7.81 Hz, 2H), 1.62 (quint, J=7.53 Hz, 2H), 1.43-1.22(br m, 6H), 0.88 (t, J=6.87 Hz, 3H)

b) Step 2: Synthesis of 1-bromo-4-[(Z)-2-chloro-2-(4-hexylphenyl) vinyl] benzene (VIb)

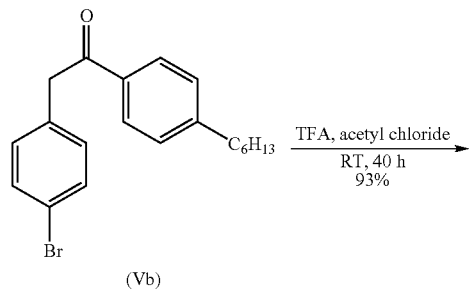

In a 2 L flask, TFA (464.17 mL; 6065.60 mmol) and acetyl chloride (344.71 mL; 4852.42 mmol) were added in one portion into 2-(4-bromo-phenyl)-1-p-tolyl-ethanone (Vb) (217.940 g; 606.56 mmol) at room temperature. Reaction mixture was vigorously stirred at room temperature for 40 h. The resulting suspension was cooled to 0° C., filtered and washed with TFA (100 mL). The white solid was dried under vacuum at 30° C. The title compound (m=209.79 g) was obtained in a 93% yield. Melting point: 52° C.

1H-NMR (CDCl3=7.26 ppm): 7.61 (d, J=3.01 Hz, 2H), 7.58 (d, J=3.01 Hz, 2H), 7.51 (d, J=8.66 Hz, 2H), 7.21 (d, J=8.47 Hz, 2H), 6.96 (s, 1H), 2.63 (t, J=7.81 Hz, 2H), 1.70-1.53(br m, 2H), 1.45-1.20(br m, 6H), 0.89 (t, J=6.87 Hz, 3H)

c) Step 3: Synthesis of 1-bromo-4-[(4-hexylphenyl) ethynyl] benzene (VIIb)

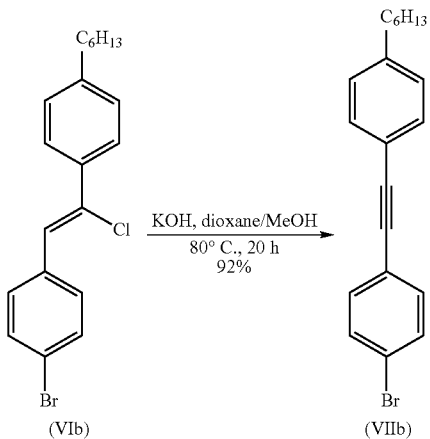

To a 2 L flask containing a solution of 1-bromo4-[(Z)-2-chloro-2-(4-hexylphenyl) vinyl] benzene (VIb) (209.79 g; 555.37 mmol) in 1,4-dioxane (1000 mL; 4.8 vols) and MeOH (300 mL; 1.4 vols), KOH (62.32 g; 1110.73 mnmol) was added in one portion. Reaction mixture was stirred at 80° C. overnight. Volume was reduced under vacuum to 200 mL and the residue was taken up in water (2000 mL). The resulting suspension was filtered and washed with water to give a clear beige solid. Drying under vacuum at 33° C. overnight gave the title compound (m=173.34 g) in a 92% yield. Melting point: 67° C. 1H-NMR (CDlC3=7.26 ppm): 7.47 (d, J=8.66 Hz, 2H), 7.43 (d, J=8.10 Hz, 2H), 7.37 (d, J=8.28 Hz, 2H), 7.16 (d, J=8.10 Hz, 2H), 2.61 (t, J=7.81 Hz, 2H), 1.59 (quint, J=7.48 Hz, 2H), 1.42-1.21 (br s, 6H), 0.88 (t, J=6.31 Hz, 3H)

d) Step 4: Synthesis of 4-(4-hexyl-phenylethynyl-benzaldehyde (Ib)

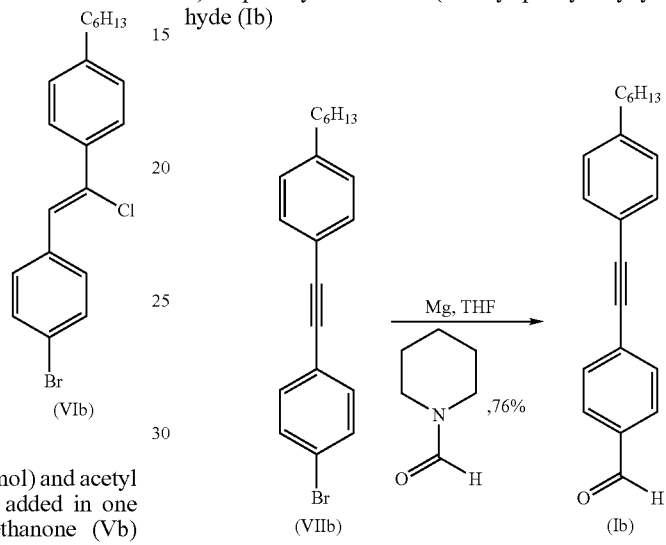

To a dry 2 L three-necked flask under a flow of $N_2$ containing magnesium turnings (13.579 g; 558.69 mmol) in dry THF (165 mL) at reflux (temperature of bath oil of 85° C.), an activating, small amount of 1-bromo-4-[(4-hexylphenyl) ethynyl] benzene (VIIb) (10.400 g; 30.474 mmol) was added in one portion. $N_2$ flow and stirring were stopped. Reaction mixture was heated at reflux for 5 minutes, then several iodine crystals were added keeping vigorous reflux to start the reaction. The reaction mixture went colorless after 5 minutes and reaction mixture turned black-green after an additional minute. A solution of the remaining amount of 1-bromo-4-[(4-hexylphenyl) ethynyl] benzene (VIIb) (162.94 g; 477.42 mmol) in dry THF (360 mL) was added drop wise over 40 minutes into the reaction mixture while keeping gentle reflux. Reflux was maintained for 20 minutes then temperature was allowed to cool to room temperature under stirring for 2 h30. The reaction mixture was cooled to 3° C. and a solution of dry 1-formyl-piperidine (84.60 mL; 761.85 mmol) in dry THF (360 mL) was added drop wise over 1 hour maintaining temperature at 5° C. (maximum temperature: 7.3° C.). The reaction mixture was then allowed to warn to room temperature and it was stirred overnight. The reaction mixture was cooled to 18° C. and 3N HCl (300 mL) was added until the solution was acidic (pH=1). Water was added (500 mL) and extraction was performed with MTBE (500 mL×3). Organic phase was washed successively with water (500 mL×2), saturated solution of $NaHCO_3$ (500 mL×1) and brine (500 mL×1). It was then dried over $MgSO_4$, filtered and concentrated to give an orange solid. It was taken up in Pet ether (400 mL) and left at 4° C. After 16 h the suspension was filtered and washed with Pet ether (2×300 mL) to give after drying under vacuum the first crop m=105.76 g. Filtrate was concentrated and taken up in Pet ether (100 mL). The resulting solid was washed with Pet ether (2×100 mL), and dried to give the second crop m=6.0 g. The title compound was obtained as a white solid (m=111.76 g) in a 76% yield. Melting point: 80° C.

1H-NMR (DMSO=2.49 ppm): 10.0 (s, 1H), 7.93 (d, J=8.28 Hz, 2H), 7.74 (d, J=8.28 Hz, 2H), 7.5 (d, J=8.28 Hz, 2H), 7.26 (d, J=8.28 Hz, 2H), 2.60 (t, J=7.81 Hz, 2H), 1.56 (quint, J=7.44 Hz, 2H), 1.36-1.16 (br s, 6H), 0.84 (t, J=6.78 Hz, 3H)

EXAMPLE 3

Preparation of 4-(4-ethyl-phenylethynyl)-benzaldehyde a) Step 1: Synthesis of 2-(4-bromophenyl)-1-(4-ethylphenyl) ethanone (Vc)

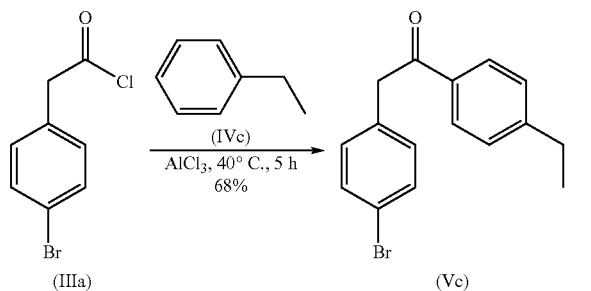

To a 50 mL three-necked flask containing AlCl3 (7.305 g; 54.79 mmol) under N$_2$, ethyl benzene (IVc) (8.40 mL; 68.48 mmol) was added in one portion at RT. To this suspension (4-bromo-phenyl)-acetyl chloride (IIIa) (10.66 g; 45.65 mmol) was added drop wise keeping temperature below 40° C. Protocol and work-up was then similar with those described above. Title compound was obtained as a white powder (m=9.923 g) in a 68% yield. Melting point: 146° C.

1H-NMR (CDCl3=7.26 ppm): 7.92 (d, J=7.91 Hz, 2H), 7.44 (d, J=8.47 Hz, 2H), 7.28 (d, J=8.10 Hz, 2H), 7.13 (d, J=8.28 Hz, 2H), 4.21 (s, 2H), 2.70 (q, J=7.59 Hz, 2H), 1.25 (t, J=7.62 Hz, 3H)

b) Step 2: Synthesis of 1-bromo-4-[(Z)-2-chloro-2-(4-ethylphenyl) vinyl] benzene (VIc)

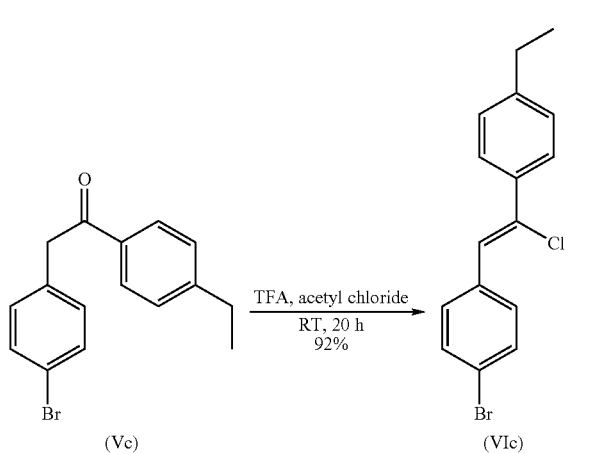

In a 100 mL flask, TFA (24.7 mL; 322.8 mmol) and acetyl chloride (18.34 mL; 258.23 rnmol) were added in one portion into 2-(4-bromophenyl)-1-(4-ethylphenyl) ethanone (Vc) (9.787 g; 32.28 mmol) at RT. Protocol and work-up was then similar with -those-described above. The title compoumd (m=9.60 g) was obtained in a 92% yield. Melting point: 75° C.

1H-NMR (CDCl3=7.26 ppm): 7.60 (d, J=7.53 Hz, 4H), 7.51 (d, J=8.66 Hz, 2H), 7.23 (d, J=8.28 Hz, 2H), 6.95 (s, 1H), 2.68 (q, J=7.59 Hz, 2H), 1.26 (t, J=7.53 Hz, 3H)

c) Step 4: Synthesis of 1-bromo-4-[(4-ethylphenyl) ethynyl] benzene (VIIc)

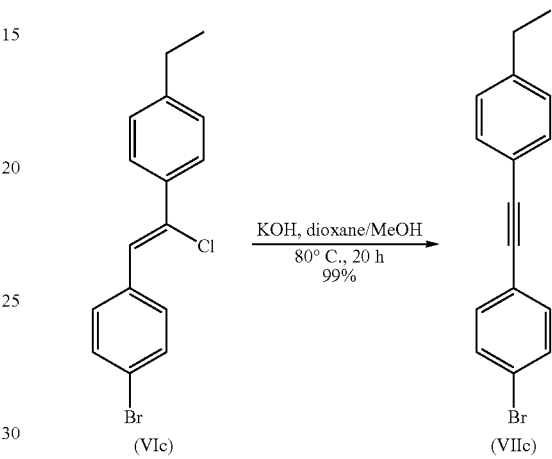

To a 100 mL flask containing a solution of 1-bromo-4-[(Z)-2-chloro-2-(4-ethylphenyl) vinyl] benzene (VIc) (9.540 g; 29.66 mmol) in 1,4-dioxane (48 mL; 5 vols) and MeOH (14 mL; 1.5 vols), KOH (3.328 g; 59.32 mmol) was added in one portion. Protocol and work-up was then similar with those described above. Title compound (m=8.39 g) was obtained in a 99% yield. Melting point: 117° C.

1H-NMR (CDCl3=7.26 ppm) : 7.47 (d, J=8.66 Hz, 2H), 7.44 (d, J=8.28 Hz, 2H), 7.37 (d, J=8.47 Hz, 2H), 7.18 (d, J=8.10 Hz, 2H), 2.66 (q, J=7.59 Hz, 2H), 1.24 (t, J=7.62 Hz, 3H)

d) Step 4: Synthesis of 4-[(4-ethylphenyl) ethynyl] benzaldehyde (Ic)

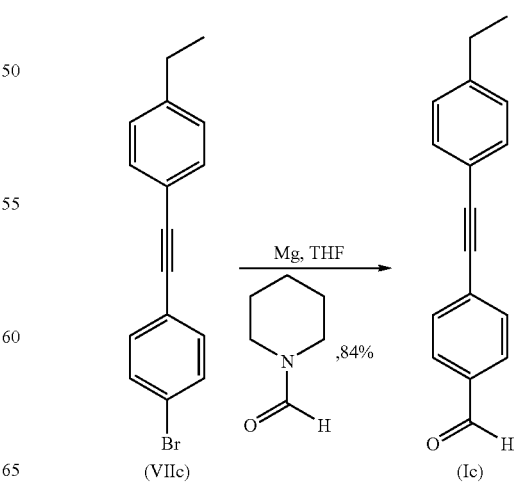

To a dry 100 mL three-necked flask under a flow of N$_2$ containing magnesium turnings (0.782 g; 32.17 mmol) in dry THF (10 mL) at reflux, an activating, small amount of 1-bromo-4-[(4-ethylphenyl) ethynyl] benzene (VIIc) (0.500 g; 1.75 mmol) was added in one portion. N$_2$ flow and stirring were stopped. Reaction mixture was heated at reflux for 5 minutes then iodine crystal was added keeping vigorous reflux to start the reaction. The reaction mixture went colourless after 5minutes and reaction mixture turned black-green after an additional minute. A solution of the remaining amount of 1-bromo-4-[(4-ethylphenyl) ethynyl] benzene (VIIc) (7.84 g; 27.49 mmol) in dry ThF (30 mL) was added drop wise into the reaction mixture while keeping gentle reflux. Reflux was maintained for 15 minutes then temperature was allowed to cool to RT under stirring for 1 h. The reaction mixture was cooled to 3° C. and a solution of dry 1-formyl-piperidine (4.12 mL; 43.87 mmol) in dry THF (25 mL) was added drop wise maintaining temperature at 5° C. The reaction mixture was then allowed to warm to room temperature (RT) and it was stirred overnight. Protocol and work-up was then similar with those described above. The title compound (m=5.77 g) was obtained as a cream solid in a 84% yield. Melting point: 89° C.

1H-NMR (CDCl3=7.26 ppm): 10.0 (s, 1H), 7.86 (d, J=8.28 Hz, 2H), 7.66 (d, J=8.28 Hz, 2H), 7.47 (d, J=8.28 Hz, 2H), 7.21 (d, J=7.91 Hz, 2H), 2.68 (q, J=7.59 Hz, 2H), 1.25 (t, J=7.62 Hz, 3H)

EXAMPLE 4

Preparation of 4-(4-chloro-phenylethynyl)-benzaldehyde a) Step 1: Synthesis of 2-(4-bromophenyl)-1-(4-chlorophenyl) ethanone (Vd)

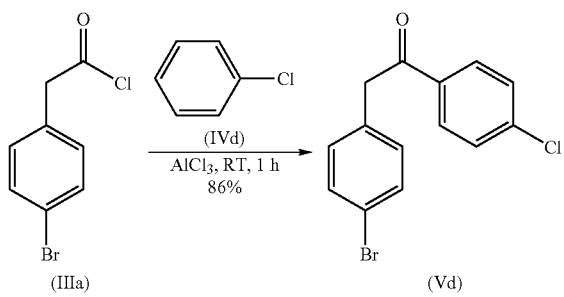

To a 100 mL three-necked flask containing AlCl$_3$ (4.797 g; 35.98 mmol) under N$_2$, chlorobenzene (IVd) (36.6 mL; 359.76 mmol) was added in one portion at RT. To this suspension (4-bromo-phenyl)-acetyl chloride (IIIa) (7.0 g; 29.98 mmol) was added in one portion without cooling. Protocol and work-up was then similar with those described above. Title compound was obtained as a white powder (m=7.99 g) in a 86% yield.

Melting point: 123° C.

1H-NMR (CDCl3=7.26 ppm): 7.92 (d, J=8.66 Hz, 2H), 7.46 (d, J=4.89 Hz, 2H), 7.43 (d, J=5.27 Hz, 2H), 7.12 (d, J=8.47 Hz, 2H), 4.21 (s, 2H)

b) Step 2: Synthesis of 1-bromo-4-[(Z)-2-chloro-2-(4-chlorophenyl) vinyl] benzene (VId)

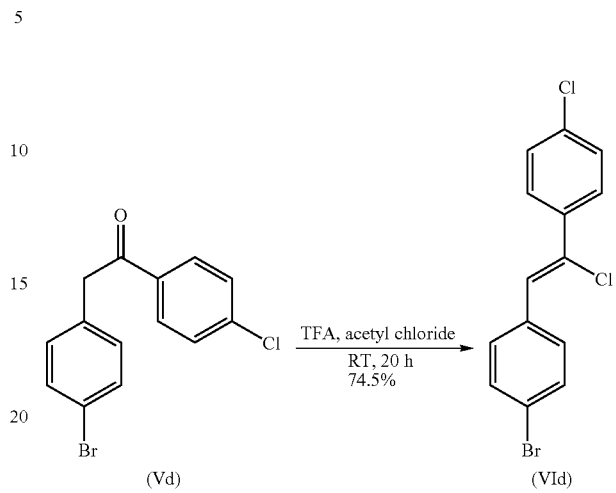

In a 250 mL flask, TFA (24.7 mL; 322.8 mmol) and acetyl chloride (18.34 mL; 258.23 mmol) were added in one portion into 2-(4-bromophenyl)-1-(4-chlorophenyl) ethanone (Vd) (10.0 g; 32.30 mmol) at RT. Protocol and work-up was then similar with those described above. The title compound (m=7.89 g) was obtained in a 74.5% yield. Melting point: 108° C.

1H-NMR (CDCl3=7.26 ppm): 7.62 (d, J=4.70 Hz, 2H), 7.59 (d, J=4.52 Hz, 2H), 7.52 (d, J=8.66 Hz, 2H), 7.37 (d, J=8.85 Hz, 2H), 6.96 (s, 1H)

c) Step 3: Synthesis of 1-bromo4-[(4-chlorophenyl) ethynyl] benzene (VIId)

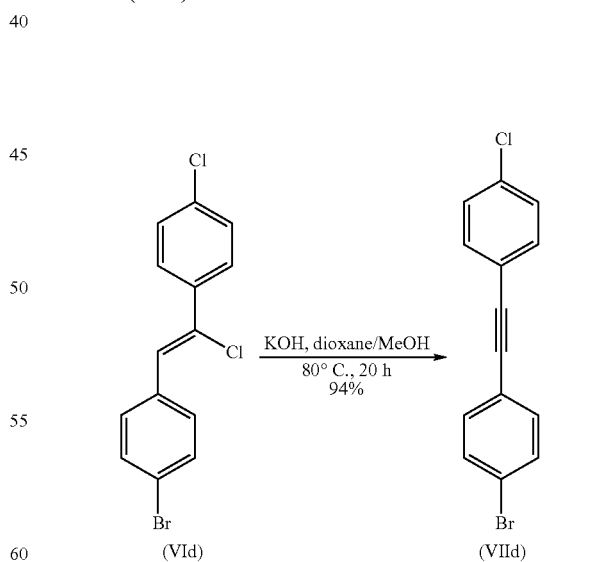

To a 100 mL flask containing a solution of 1-bromo-4-[(Z)-2-chloro-2-(4-chloro-phenyl) vinyl] benzene (VId) (7.89 g; 24.05 mmol) in 1,4-dioxane (40 mL; 5 vols) and MeOH (12 mL; 1.5 vols), KOH (2.699 g; 48.10 mmol) was added in one portion. Protocol and work-up was then similar with those described above. Title compound (m=6.598 g) was obtained in a 94% yield. Melting point: 179° C.

1H-NMR (CDCl3=7.26 ppm): 7.48 (d, J=8.47 Hz, 2H), 7.44 (d, J=8.66 Hz, 2H), 7.37 (d, J=8.47 Hz, 2H), 7.32 (d, J=8.66 Hz, 2H)

d) Step 4: Synthesis of 4-[(4-chlorophenyl)ethynyl]benzaldehyde (Id)

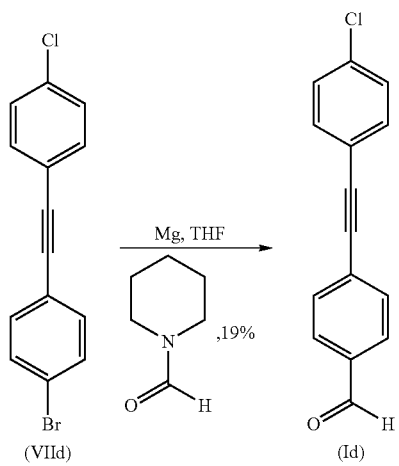

To a dry 100 mL three-necked flask under a flow of N₂ containing magnesium turnings (0.595 g; 24.50 mmol) in dry THF (10 mL) at reflux, an activating, small amount of 1-bromo-4-[(4-chlorophenyl) ethynyl] benzene (VIId) (0.39 g; 1.33 mmol) was added in one portion. N₂ flow and stirring were stopped. Reaction mixture was heated at reflux for 5 minutes then iodine crystal was added keeping vigorous reflux to start the reaction. The reaction mixture went colourless after 5 minutes and reaction mixture turned black-blue after an additional minute. A solution of the remaining amount of 1-bromo-4-[(4-chlorophenyl) ethynyl] benzene (VIId) (6.104 g; 20.93 mmol) in dry THF (35 mL) at 55° C. was added drop wise into the reaction mixture while keeping gentle reflux. Reflux was maintained for 15 minutes then temperature was allowed to cool to RT under stirring for 1 h. The reaction mixture was cooled to 3° C. and a solution of dry 1-formyl-piperidine (3.71 mL; 33.40 mmol) in dry THF (10 mL) was added drop wise maintaining temperature at 5° C. The reaction mixture was then allowed to warm to RT and it was stirred overnight. Protocol and work-up was then similar with those described above. Purification was performed by flash chromatography (SiO₂) using (cyclohexane 9-ethyl acetate 1). The title compound (m=1.02 g) was obtained as a white solid in a 19% yield. Melting point: 164° C.

1H-NMR (CDCl3=7.26 ppm): 10.0 (s, J=– Hz, 1H), 7.87 (d, J=8.28 Hz, 2H), 7.66 (d, J=8.10 Hz, 2H), 7.48 (d, J=8.47 Hz, 2H), 7.35 (d, J=8.47 Hz, 2H)

EXAMPLE 5

Preparation of 4-(4-butyl-phenylethynyl)-benzaldehyde a) Step 1: Synthesis of 2-(4-bromophenyl)-1-(4-butylphenyl) ethanone (Ve)

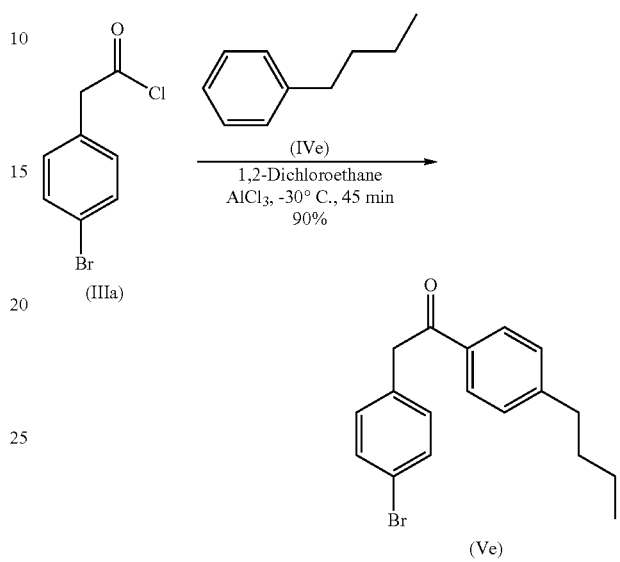

To a 1 L three-necked flask containing AlCl₃ (40 g, 0.299 mol) in 1,2-dichloroethane (600 mL) under N₂, butylbenzene (IVe) (49.7 mL, 0.299 mol) was added in one portion at −30° C. To this suspension (4-bromo-phenyl)-acetyl chloride (IIIa) (70 g, 0.299 mol) was added slowly over a period of 30min at such a rate that the internal temperature did not rise above −30° C. The reaction mixture was stirred at this temperature for 45 min and poured into an ice-cold solution of 1.5M HCl (1000 ml). The product was extracted into dichloromethane (2×500 ml), washed with 10% sodium bicarbonate solution (500 ml), water, brine and dried over Na₂SO₄. The solvent was evaporated under reduced pressure to obtain the titled compound as a white powder (m=90 g) in a 90.9% yield.

Melting point: 129.4° C.-131.1° C.

1H-NMR (CDCl3=7.26 ppm): 1H-NMR 7.92 (d, J=8.16 Hz, 2H), 7.45 (d, J=8.28 Hz, 2H), 7.27 (d, J=8.22 Hz, 2H), 7.14 (d, J=8.19 Hz, 2H), 4.22 (s, 2H), 2.67 (t, J=7.47 Hz, 2H), 1.62 (m, J=7.38 Hz, 2H), 1.37 (m, 2H), 0.93 (t, J=7.29 Hz, 3H)

b) Step 2: Synthesis of 1-bromo-4-[(Z)-2-chloro-2-(4-butylphenyl) vinyl] benzene (VIe)

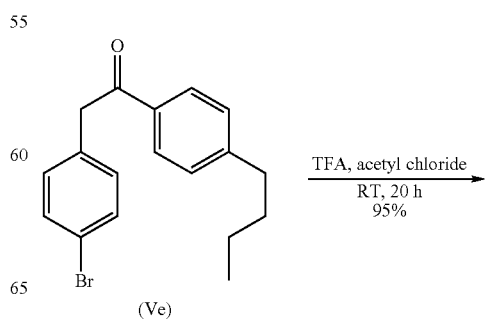

-continued

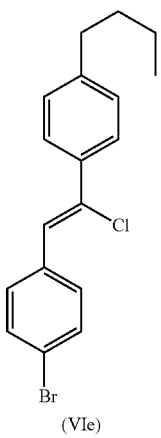
(VIe)

To a 2 L three-necked flask containing TFA (231 mL, 3.01 mol) and acetyl chloride (171.4 mL, 2.41 mol) was added in one portion 2-(4-bromophenyl)-1-(4-butylphenyl) ethanone (Ve) (100 g; 0.301 mol) at RT. The reaction mixture was stirred at room temperature overnight and work-up was then similar with those described above. The title compound (m=100 g) was obtained in a 95% yield. Melting point: 59-61° C.

1H-NMR (CDCl3=7.26 ppm): 7.6 (m, , 4H), 7.52 (d, J=8.4 Hz, 2H), 7.22 (d, J=8.01 Hz, 2H), 6.97 (s, 1H), 2.65 (t, J=7.59 Hz, 2H), 1.63 (m, J=7.41 Hz, 2H), 1.37 (m, 2H), 0.95 (t, J=7.35 Hz, 3H)

c) Step 3: Synthesis of 1-bromo4-[(4-butylphenyl) ethynyl] benzene (VIIe)

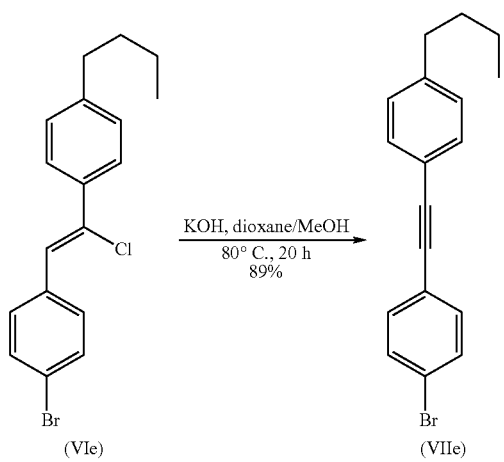

To a 1 L flask containing a solution of 1-bromo-4-[(Z)-2-chloro-2-(4-butyl-phenyl) vinyl] benzene (VIe) (100 g; 0.285 mol) in 1,4-dioxane (500 mL; 5 vols) and MeOH (200 mL; 2vols), KOH (32 g; 0.571 mol) was added in one portion. Protocol and work-up was then similar with those described above. Title compound (m=80 g) was obtained in a 89% yield. Melting point: 75.6-76.1° C.

1H-NMR (CDCl3=7.26 ppm): 7.4 (m,, 6H), 7.17 (d, J=7.8 Hz, 2H), 2.63 (t, J=7.56 Hz, 2H), 1.63 (m, J=7.38 Hz, 2H), 1.38 (m, 2H), 0.95 (t, J=7.2 Hz, 3H)

d) Step 4: Synthesis of 4-[(4-butylphenyl) ethynyl] benzaldehyde (Ie)

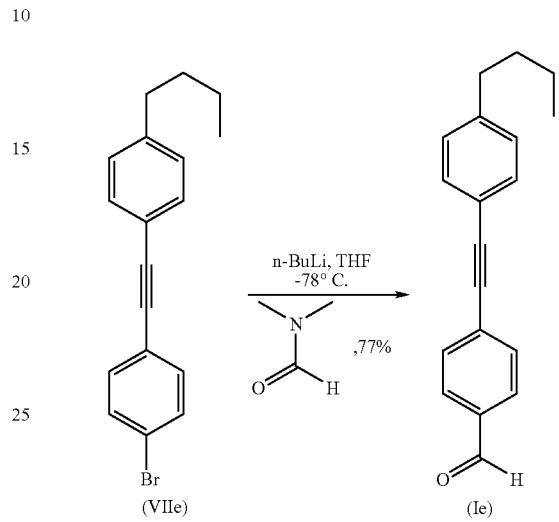

To a dry 2 L three-necked flask under a flow of $N_2$ containing 1-bromo-4-[(4-butylphenyl) ethynyl] benzene (VIIe) (100 g; 0.319 mol) in dry THF (1000 mL) at −78° C. was added n-BuLi (2.5M in hexane, 153.25 mL, 0.383 mol) and the reaction mixture was stirred at this temperature for 2 h. The reaction mixture went dark-green after 5 minutes of the addition of butyl lithium. To this reaction mixture was added DMF (29.56 mL, 0.383 mol) and the resulting mixture was stirred for an additional 1 h at −78° C. The reaction mixture turned black-blue after the addition of DMF. The reaction mixture was then quenched with 1.5M HCl (750 ml) at this temperature and the product was extracted with MTBE (3×500 mL). The combined organic layer were washed with 10% sodium bicarbonate solution (500 ml), water, brine and dried. The solvent was evaporated under reduced pressure to afford the title compound (m=65 g) as a white solid in a 77% yield. Melting point: 76-78° C.

1H-NMR (CDCl3=7.26 ppm): 10.02 (s, 1H), 7.86 (d, J=7.47 Hz, 2H), 7.66 (d, J=7.98 Hz, 2H), 7.47 (d, J=7.2 Hz, 2H), 7.19 (d, J=7.68 Hz, 2H), 2.64 (t, J=7.5 Hz, 2H), 1.63 (quint, J=7.2 Hz, 2H), 1.36 (m, 2H), 0.94 (t, J=7.2 Hz, 3H)

The following further compounds may be obtained using the above set out protocols Example 6: 4-p-Tolylethynyl-benzaldehyde
Example 7: 4-(4-Propyl-phenylethynyl)-benzaldehyde
Example 8: 4-(4-Cyclohexyl-phenylethynyl)-benzaldehyde
Example 9: 4-(4-Propoxy-phenylethynyl)-benzaldehyde
Example 10: 4-(4-Phenoxy-phenylethynyl)-benzaldehyde
Example 11: 4-Biphenyl4-ylethynyl-benzaldehyde

The invention claimed is:
1. A process for the preparation of compounds of formula (I):

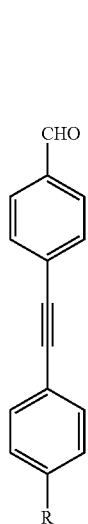
(I)

wherein R is $C_1$-$C_{12}$-alkyl, $C_1$-$C_{12}$-alkyl aryl, $C_1$-$C_{12}$-alkyl heteroaryl, $C_2$-$C_{12}$-alkenyl, $C_2$-$C_{12}$-alkenyl aryl, $C_2$-$C_{12}$-alkenyl heteroaryl, $C_2$-$C_{12}$-alkynyl, $C_2$-$C_{12}$-alkynyl aryl, $C_2$-$C_{12}$-alkynyl heteroaryl, $C_1$-$C_{12}$-alkyl-$C_3$-$C_8$-cycloalkyl, $C_3$-$C_8$-cycloalkyl, $C_1$-$C_{12}$-alkoxy, aryl, heteroaryl, or a halide;

said process comprising the steps of:

Step 1: reacting an acyl chloride of formula (III) with an alkyl benzene of formula (IV) to yield the corresponding compound (V):

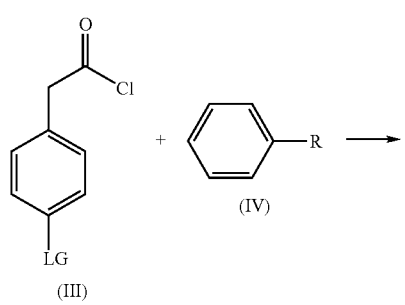

wherein LG is a leaving group;

Step 2: transforming a compound of formula (V) into compound of formula (VI), using a suitable halogenating agent:

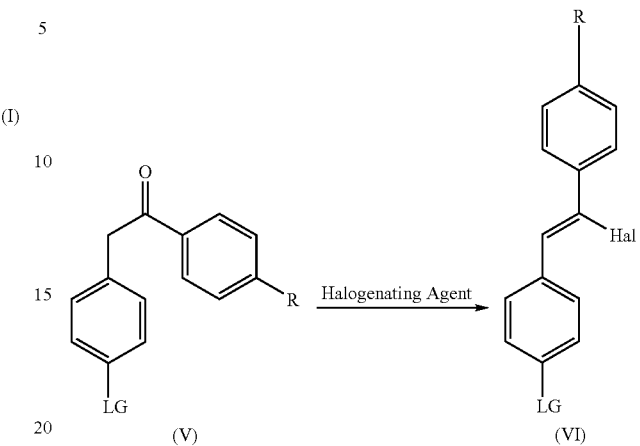

Step 3: subjecting a compound (VI) to an elimination reaction to provide a compound of formula (VII):

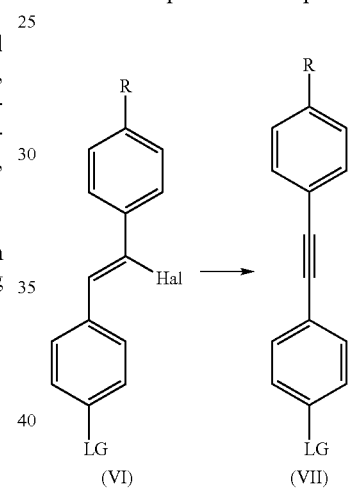

Step 4: subjecting a compound of formula (VII) or an activated species thereof with a formylating agent (VIII) for giving the compound (I):

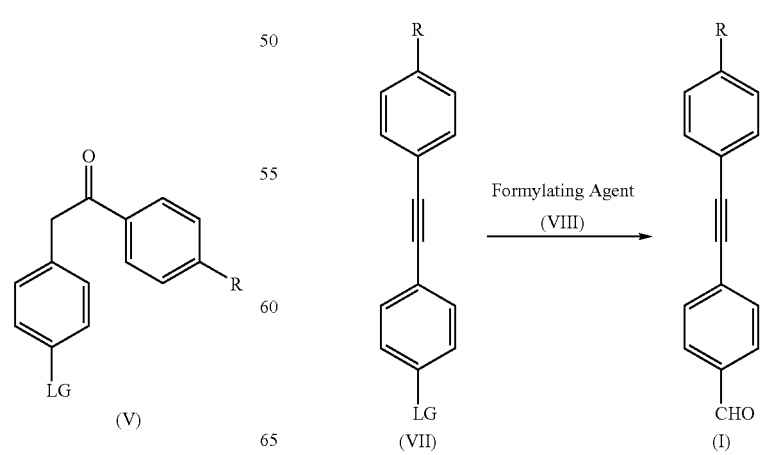

2. The process according to claim 1, wherein the reaction of step 1 is conducted in the presence of $AlCl_3$.

3. The process according to claim 1, wherein the halogenating agent in step 2 is acetyl chloride.

4. The process according to claim 1, wherein the reaction of step 3 is performed in presence of a base.

5. The process according to claim 1, wherein the formylating agent in step 4 is selected from the group consisting of DMF, 1-formyl-piperidine, 1-formyl piperazine, N-methyl-N-(2-pyridyl) formamide, N-methyl formanilide, and Weinreb formamide.

6. The process according to claim 1, wherein the reaction of step 4 is conducted in the presence of magnesium or butyl lithium.

7. The process according to claim 1, wherein R is $C_1$-$C_6$ alkyl.

8. The process according to claim 1, wherein the compound is selected from the group consisting of:
   4-(4-methoxy-phenylethynyl)-benzaldehyde;
   4-(4-hexyl-phenylethynyl)-benzaldehyde;
   4-(4-ethyl-phenylethynyl)-benzaldehyde;
   4-(4-chloro-phenylethynyl)-benzaldehyde;
   4-(4-butyl-phenylethynyl)-benzaldehyde;
   4-p-tolylethynyl-benzaldehyde;
   4-(4-propyl-phenylethynyl)-benzaldehyde;
   4-(4-cyclohexyl-phenylethynyl)-benzaldehyde;
   4-(4-propoxy-phenylethynyl)-benzaldehydel;
   4-(4-phenoxy-phenylethynyl)-benzaldehyde; and
   4-biphenyl-4-ylethynyl-benzaldehyde.

9. The process according to claim 1, wherein LG is a halide.

10. The process according to claim 1, wherein the reaction of step 1 is performed in the presence of $FeCl_3$.

11. The process according to claim 1, wherein the reaction of step 1 is performed at a temperature in a range from room temperature to 50° C. for a period of about 5 hours.

12. The process according to claim 1, wherein the halogenating agent in step 2 is bromide.

13. The process according to claim 1, wherein the reaction of step 2 is performed at room temperature for a period of 40 hours.

14. The process according to claim 1, wherein the reaction of step 3 is performed at a temperature of 80° C. for a period of 20 hours.

* * * * *